US005834420A

United States Patent [19]

Laub et al.

[11] Patent Number: 5,834,420

[45] Date of Patent: Nov. 10, 1998

[54] FIBRINOGEN CONCENTRATE OBTAINED FROM BLOOD PLASMA, PROCESS AND PLANT FOR ITS PREPARATION

[75] Inventors: Ruth Laub, Brussels; Luc De Wael, Ranst, both of Belgium

[73] Assignee: Croix-Rouge de Belgique, Brussels, Belgium

[21] Appl. No.: 765,838

[22] PCT Filed: Jul. 14, 1995

[86] PCT No.: PCT/BE95/00069

§ 371 Date: Jul. 7, 1997

§ 102(e) Date: Jul. 7, 1997

[87] PCT Pub. No.: WO96/02571

PCT Pub. Date: Feb. 1, 1996

[30] Foreign Application Priority Data

Aug. 23, 1995 [EP] European Pat. Off. .............. 94870121

[51] Int. Cl.[6] ............................ A61K 35/14; C07K 1/00; C07K 14/00; C07K 17/00

[52] U.S. Cl. ............................... 514/2; 530/382; 530/383

[58] Field of Search ................................... 530/383, 382; 514/2

[56] References Cited

U.S. PATENT DOCUMENTS

| | | | |
|---|---|---|---|
| 4,295,855 | 10/1981 | Sasaki | 530/382 |
| 4,297,344 | 10/1981 | Schwinn et al. | 424/101 |
| 4,789,733 | 12/1988 | Winkelmann | 530/383 |
| 5,099,003 | 3/1992 | Kotitschke | 530/382 |
| 5,252,709 | 10/1993 | Burnouf | 530/382 |

FOREIGN PATENT DOCUMENTS

| | | |
|---|---|---|
| 0018561 | 11/1980 | European Pat. Off. . |
| 0555135 | 2/1993 | European Pat. Off. . |
| 3001435 | 7/1980 | Germany . |
| 0131740 | 1/1985 | WIPO . |
| 8605190 | 9/1986 | WIPO . |
| 9602571 | 2/1996 | WIPO . |

*Primary Examiner*—Cecilia J. Tsang
*Assistant Examiner*—S. G. Marshall
*Attorney, Agent, or Firm*—Knobbe, Martens, Olson and Bear, LLP

[57] ABSTRACT

A fibrinogen concentrate has a purity of 98% or higher and is free of viral contaminants and proteases. The fibrinogen concentrate is obtained by subjecting a solubilized plasma fraction containing fibrinogen to a viral inactivation chemical treatment using a solvent/detergent, subjecting the resulting viral-inactivated fraction to precipitation in a solution containing an amino acid at an acidic pH to obtain a supernatant, filtering the supernatant to obtain a purified fibrinogen concentrate, and recovering the purified fibrinogen concentrate.

16 Claims, 6 Drawing Sheets

FIBRINOGEN CONCENTRATE OBTAINED FROM BLOOD PLASMA, PROCESS AND PLANT FOR ITS PREPARATION

This application is a 371 of PCT/BE95/0069.

SUBJECT OF THE INVENTION

The present invention relates to a fibrinogen concentrate obtained from human or animal blood plasma and to the process for its preparation, as well as to the plant for preparing the said fibrinogen concentrate.

The present invention furthermore relates to the pharmaceutical and/or cosmetic composition which comprises the said fibrinogen concentrate.

TECHNOLOGICAL BACKGROUND UNDERLYING THE INVENTION

Fibrinogen is a plasma protein which is of fundamental importance in the coagulation process, and its areas of pharmaceutical or cosmetic application cover a variety of fields (wound healing, coagulating agent, constituent of biological adhesives, fibrinogenaemia, inhibition of operative and post-operative sequelae, etc.).

Making blood proteins such as fibrinogen available requires, for the said proteins to be used for therapeutic or non-therapeutic purposes, purification techniques which make it possible to obtain products which are of high purity and completely free from viral contaminants (HIV, hepatitis viruses, parvovirus, etc.) or from biological molecules such as antibodies or proteases (65/65 EEC, 75/319/EEC & 89/381 EEC Council Directives).

For this reason, various treatment methods (filtration, precipitation, affinity chromatography, etc.) have been proposed for eliminating or inactivating plasma contaminants and/or compounds which are derived from the plasma (factor VIII, von Willebrand factor, fibronectin, etc.).

The treatments for inactivating viruses may consist of a thermal treatment or a chemical treatment.

A chemical treatment may, for example, consist of a viral inactivation which is brought about by using a solvent/detergent such as described in Patent Application No. EP-0 131 740.

However, these thermal or chemical treatments for inactivating viruses do not completely eliminate some viral contaminants, in particular some non-enveloped viruses such as parvovirus B19.

STATE OF THE ART

Patent Application PCT/FR89/00050 (WO89/12065) describes such a viral inactivation using a solvent/detergent in a process for separating plasma proteins from a solubilized fraction of a plasma cryoprecipitate.

According to this process, the fraction of a plasma cryoprecipitate, which fraction is resolubilized in water, is subjected to a solvent/detergent viral inactivation treatment and then to a single chromatographic separation on an anion exchange resin whose matrix is a gel which is able, by virtue of its porosity and hydrophobicity properties, to retain the factor VIII/von Willebrand factor complex. Each of the proteins is then recovered selectively by means of successive increases in the ionic strength of the elution buffer.

While the first filtrate from the chromatography principally contains fibrinogen, it also contains albumin, immunoglobulins and viral inactivation agents (Tween and TNBP).

Using this solution, the fibrinogen is then purified (elimination of the viral inactivation agents) by means of a fresh chromatography step on a column of heparin/sepharose resin.

The collected fibrinogen fraction is then concentrated and dialysed using a cassette system. The concentrated product is apportioned into bottles and lyophilized.

However, this technique for purifying fibrinogen suffers from the drawback that it requires a chromatographic purification step which is both complex and expensive.

Furthermore, this purification technique does not allow substantial volumes of fractions which are enriched in high-purity fibrinogen to be treated rapidly on an industrial scale. Again, the fibrinogen concentrate which is purified by means of an additional chromatographic step will lack factor XIII, thereby making it less useful as a biological adhesive.

Patents and Patent Applications DE-30 01 435, EP-0 311 950 and PCT/GB86/00121 (WO86/05190) describe processes for purifying blood compounds derived from blood plasma fractions by means of precipitation at acid pH and in the presence of an amino acid.

These processes can be combined with a chemical viral inactivation process.

Nevertheless, the products which are obtained by means of the various techniques mentioned are not sufficiently pure.

Thus, contaminants such as proteases are not eliminated by means of these techniques.

Furthermore, the non-delipidated fibrinogen concentrate which is obtained can be solubilized only very slowly.

OBJECTS OF THE INVENTION

The present invention aims to obtain a fibrinogen concentrate which is highly purified and which lacks (enveloped and/or non-enveloped) viral contaminants and biological molecules such as proteases.

Another object of the present invention is to obtain a fibrinogen concentrate which can easily be solubilized, preferably in less than 10 minutes.

A supplementary object of the present invention is also to obtain a fibrinogen concentrate which is not free from factor XIII, so as to ensure its application as a biological adhesive.

The present invention also aims to achieve a process for obtaining this fibrinogen concentrate derived from blood plasma, which process does not suffer from the drawbacks of the abovementioned state of the art, in particular a process which is simple, rapid and inexpensive and which allows substantial volumes of highly purified fibrinogen to be obtained industrially.

CHARACTERISTIC ELEMENTS OF THE INVENTION

The Applicant has succeeded in isolating a fibrinogen concentrate which lacks all the currently known viral contaminants, namely the known enveloped and non-enveloped viruses, in particular the hepatitis A, hepatitis B and hepatitis C viruses, the HIV viruses and the parvoviruses (in particular parvovirus B19).

Furthermore, the said fibrinogen concentrate is characterized by a purity which is particularly high, being greater than 95%, if not greater than 98%. The residual fraction in this fibrinogen concentrate consists of factor XIII (it being possible for the proportion of factor XIII in the residual fraction to be greater than 30%) and immunoglobulins.

In addition, a very low concentration of chemical additives (solvents/detergents), which are used in the process for chemically inactivating this fibrinogen concentrate, can also remain in this fibrinogen concentrate.

However, the solvents/detergents which are detected in the final product are present only as non-toxic traces.

Advantageously, the said fibrinogen concentrate is also free from proteases.

Advantageously, the said fibrinogen concentrate according to the invention is delipidated, that is to say it can be rapidly and easily solubilized in a few minutes, preferably in less than 15 minutes, if not less than 10 minutes.

Furthermore, the fibrinogen concentrate does not coagulate after having been kept at 4° C. for more than 12 months.

Preferably, the said fibrinogen concentrate comprises more than 0.001%, preferably more than 0.1%, of factor XIII.

The present invention also relates to the process for obtaining the fibrinogen concentrate in which a solubilized plasma fraction containing the fibrinogen is subjected to a chemical viral inactivation treatment and to one or more steps of precipitation in a solution which is at acid pH and which contains an amino acid (and, where appropriate, to one or more physical viral inactivation treatments (treatments with ultraviolet, in particular UVC, radiation) or thermal viral inactivation treatments).

The combination of these different steps unexpectedly renders it possible, by means of a synergistic effect, to obtain the fibrinogen concentrate according to the invention whose purity is greater than 95% and which is free from viral contaminants.

Advantageously, the step involving precipitation at acid pH is carried out at a pH which is between 4.0 and 7.0, preferably between 5.5 and 6.5.

The concentration of amino acid (preferably glycine) in the solution is between 0.1 and 3.3 molar, preferably between 0.5 and 1.5 molar.

In addition, the purification process includes, preferably after each precipitation step, one or more steps in which the purified fibrinogen is filtered. Preferably, this filtration step is carried out through a filter of activated carbon.

The AKS-4 or AKS-7 carbon filters, such as those supplied by Zeiss, are particularly suitable for the process of the invention.

According to the invention, the chemical viral inactivation treatment consists of a solvent/detergent treatment such as described in Patent Application EP-0 131 740.

The thermal viral inactivation step is carried out, for example, by heating at a temperature which is greater than 80° C. for a period which is greater than or equal to 10 hours, and which is preferably between 24 and 72 hours.

The physical viral inactivation step is carried out by treating the solubilized plasma fraction with ultraviolet C rays whose wavelength is between 250 and 270 nm, preferably of the order of 254 nm, with the irradiation doses being of the order of 250 joules/$m^2$.

According to the invention, the solubilized plasma fraction is selected from the group consisting of the solubilized fraction of a plasma cryoprecipitate, the Cohn FI fraction and/or a mixture of these fractions.

According to a first preferred embodiment of the invention, the solubilized fraction of a plasma cryoprecipitate is first of all subjected to a single step of chromatography on an ion exchange resin.

Preferably, the ion exchange resin comprises a matrix which consists of a gel which is able, by virtue of its porosity and hydrophobicity properties, to retain the factor VIII/von Willebrand factor complex which is present in the plasma.

In addition, in accordance with this preferred embodiment of the invention, the process also includes a step in which the solubilized fraction of the plasma cryoprecipitate is first of all subjected to a prepurification treatment which comprises a treatment with aluminium hydroxide and/or a precipitation at a temperature which is between 10° and 20° C.

The present invention also relates to the pharmaceutical and/or cosmetic composition which comprises the fibrinogen concentrate according to the invention and/or is obtained by the acquisition process according to the invention.

In particular, this pharmaceutical and/or cosmetic composition is a biological adhesive which is as described in Patent Application EP-0 305 243 and which comprises the fibrinogen concentrate according to the invention.

A final aspect of the present invention relates to the plant for preparing a blood derivative, in particular a blood fibrinogen concentrate, a pharmaceutical or cosmetic composition and/or a biological adhesive according to the invention. The said plant includes a device which ensures physical inactivation of the viruses in the solubilized plasma fraction in accordance with the process of the invention.

In particular, the device of the plant of the invention includes a UVC ray emitter whose wavelength is between 250 and 270 nm, preferably of the order of 254 nm, with the emitter emitting at irradiation doses of the order of 250 joules/$m^2$.

Figure 1:
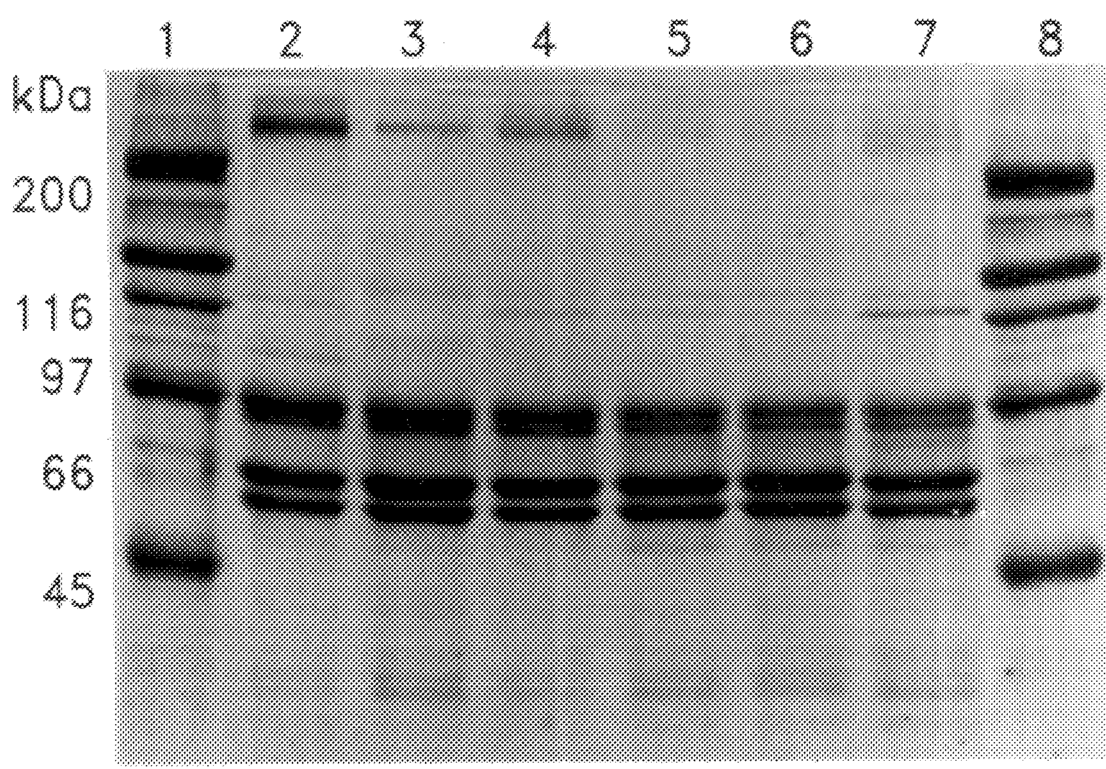
FIG. 1 represents a densitometric analysis, on a polyacrylamide (SDS-PAGE) gel, of the purified fibrinogen using various methods.

The present invention will be described in more detail, while referring to the attached figures, in the following examples, which are given by way of illustration and without limiting the invention.

EXAMPLE 1

A resuspended plasma cryoprecipitate containing fibrinogen is used as the starting material.

This cryoprecipitate suspension is subjected to a prepurification involving treatment with aluminium hydroxide and precipitation in the cold.

This prepurified solution is then subjected to a solvent/detergent viral inactivation treatment as described in European Patent Application EP-0 131 740.

This solubilized fraction is then subjected to a single step of chromatography on an ion exchange resin and the first fraction obtained (eluate+washing volume) is recovered selectively, with this fraction being purified by means of a first precipitation step carried out under the following conditions:

temperature=25° C.
0.15M Na citrate, 0.15M NaCl, 1M glycine
pH 6.1 (1 normal HCl)
1M glycine.

After that, the temperature is brought to +4° C. and a centrifugation is carried out.

The precipitate is redissolved under the following conditions:

pH 7.0 temperature=30° C.

0.15M Na citrate, 0.15M NaCl, 1M glycine

AKS-4/AKS-7 filtration pH 6.1 (1 normal HCl).

After that, the temperature is brought to +4° C. and a centrifugation is carried out.

The precipitate is redissolved under the following conditions:

temperature=30° C.

0.05M Na citrate, 50 g/l glucose 0.05M NaCl pH 7.

The precipitate is subsequently filtered through a carbon filter of the AKS4-EKSP® type (SEITZ), and then concentrated and subjected to diafiltration. The concentrated product is subsequently sterilized by filtration, after a stabilizer (sucrose) has been added, and then placed in bottles and lyophilized.

The yields which are obtained in accordance with the process of the invention are of the order of 80%, and the purity of the products achieves values of the order of 98%±2%.

EXAMPLE 2

A plasma cryoprecipitate which has been subjected to a chemical solvent/detergent viral inactivation treatment is used as the starting material, as in Example 1; however, this is done without subjecting the cryoprecipitate to a chromatographic prepurification step as in Example 1.

The fibrinogen is purified by one single precipitation step. The yields which are obtained are of the order of from 70 to 80%, and the purity of the products achieves values of the order of from 75 to 85%.

Table 1 below summarizes the comparative data from different methods of purifying the fibrinogen.

TABLE 1

| | Overall yield % | Purity % (e) | Tween 80 ppm (f) | TNBP pp (g) | Proteases (h) |
|---|---|---|---|---|---|
| Method I (a) | 70–80 | >98 | <10 | <1 | – |
| Method II (b) | 70–80 | 75–85 | 125 | <20 | ++ |
| Method III (c) | >90 | >90 | 82 | <10 | ± |
| Method IV (d) | nd | 70–80 | nd | nd | ++ |

(a) The fibrinogen is purified from the first fraction which is obtained selectively from a single chromatographic step, followed by 2 glycine precipitations and filtration through an AKS4-EKSP® filter (Example 1).

(b) The fibrinogen is purified from a plasma cryoprecipitate which is not pretreated by chromatography, and purified by a single precipitation (Example 2).

(c) The process is identical to process (a) except that it includes only a single glycine precipitation.

(d) The fibrinogen is purified in accordance with the process described in Patent Application PCT/FR89/00050.

(e) Densitometric analysis of the polyacrylamide gel (SDS-PAGE, see FIG. 1).

(f) The acceptable upper limit for the concentration of Tween 80 should be less than 100 ppm.

(g) The acceptable upper limit for the concentration of TNBP should be less than 10 ppm.

Figure 2:
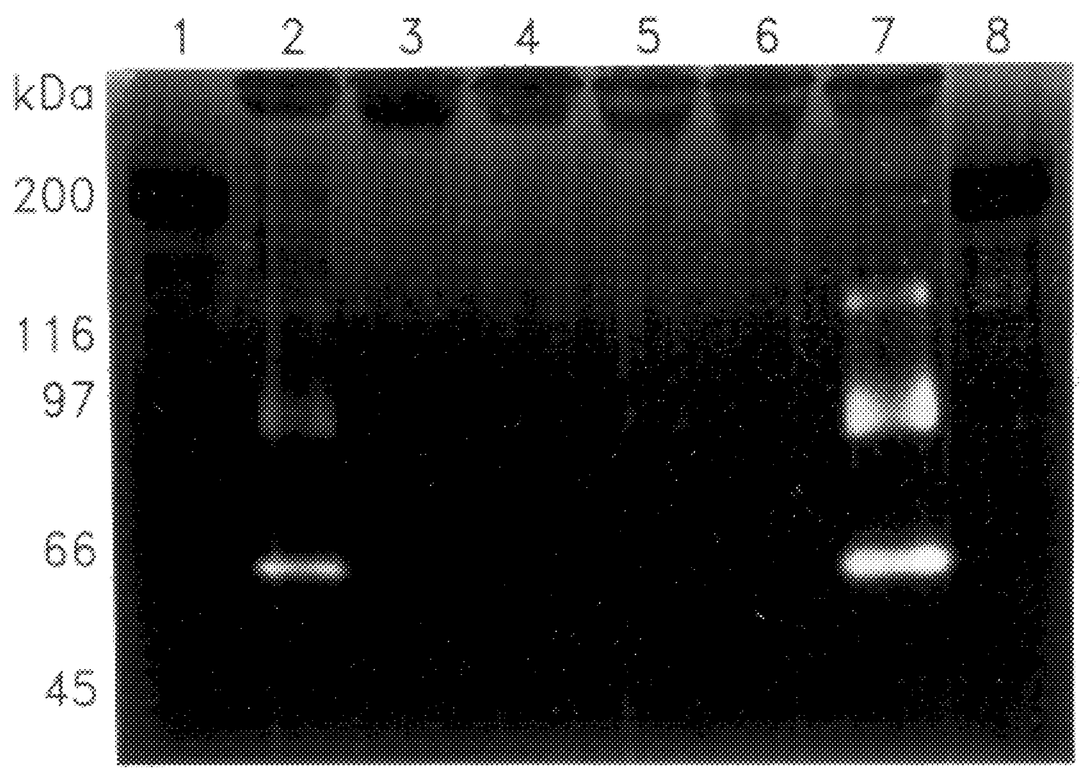
FIGS. 2 to 5 represent a zymographic analysis of the purified fibrinogen using various methods.
Figure 3:
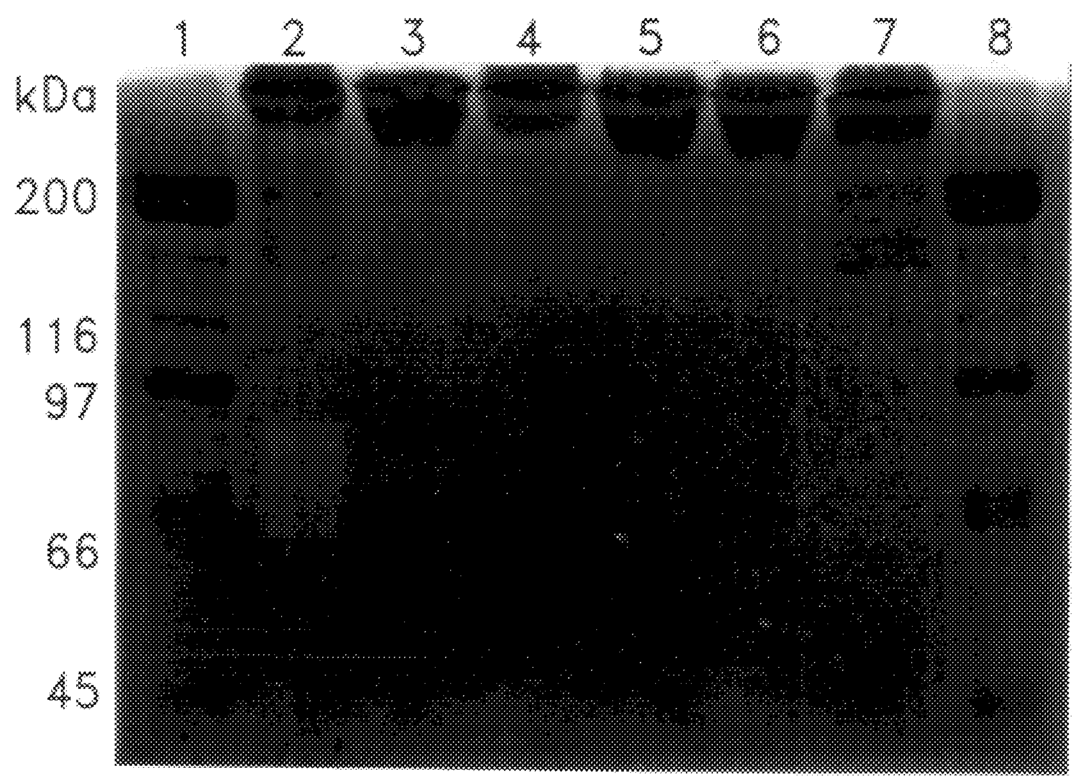
Figure 4:
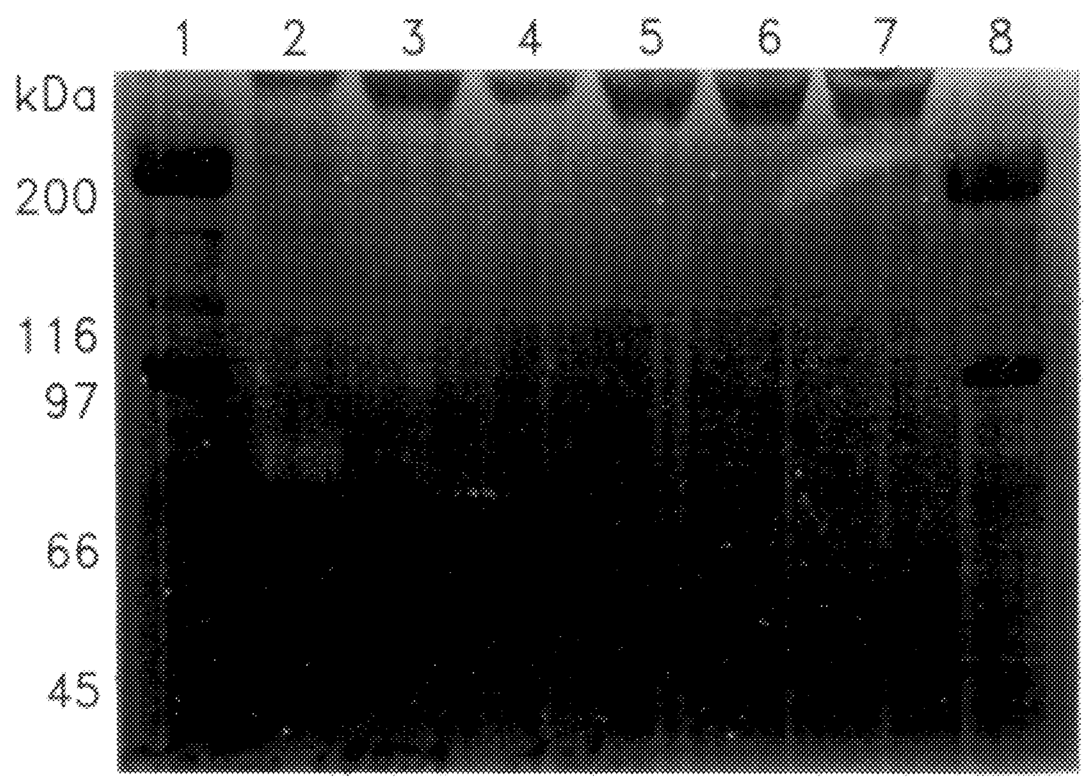
Figure 5:
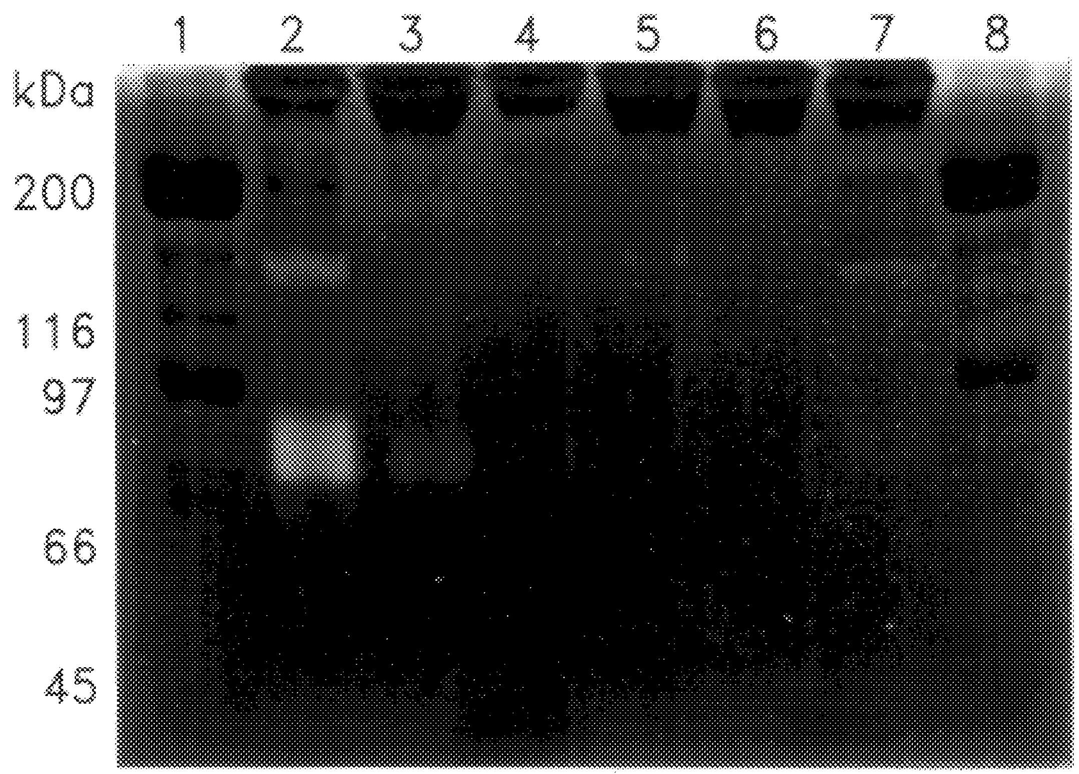

(h) The presence of proteases was demonstrated by zymographic analysis (see FIG. 2).

The polyacrylamide gel (SDS-PAGE) densitometric analysis in FIG. 1 depicts different batches of fibrinogen which were obtained using different processes according to the invention and according to the state of the art.

Quantity of material deposited per track: 5 μg of protein

Tracks 1 and 8: BIO-RAD® "High Range" molecular weight standards

Track 2: solution of the cryoprecipitate

Track 3: fibrinogen standard from Kordia®

Track 4: fibrinogen prepared from the cryoprecipitate (2 glycine precipitations)

Track 5: fibrinogen prepared from peak A of an ion exchange column (1 glycine precipitation)

Track 6: fibrinogen prepared from peak A of an ion exchange column (2 glycine precipitations)

Track 7: fibrinogen prepared from a heparin-sepharose (Pharmacia) column

Tracks 2, 3, 4 and 7 include an additional band (300,000 MW) of fibronectin.

The zymographic analysis presented in FIGS. 2 to 5 depicts the analysis of different fibrinogen batches which were obtained using different processes according to the invention and according to the state of the art (on gelatin (FIG. 2), on gelatin+EDTA (FIG. 3), on casein (FIG. 4) and on casein+EDTA (FIG. 5)).

Quantity of material deposited per track: 500 μg of protein

Tracks 1 and 8: BIO-RAD® "High Range" molecular weight standards

Track 2: solution of the cryoprecipitate

Track 3: fibrinogen standard from Kordia®

Track 4: fibrinogen prepared from the cryoprecipitate (2 glycine precipitations)

Track 5: fibrinogen prepared from peak A of an ion exchange column (1 glycine precipitation)

Track 6: fibrinogen prepared from peak A of an ion exchange column (2 glycine precipitations)

Track 7: fibrinogen prepared from a heparin-sepharose (Pharmacia) column

Tracks 2 and 7 clearly indicate the presence of proteases.

EXAMPLE 3

Preparation of Fibrinogen Concentrate from the FI Fraction (Cohn Fractionation (see Tables 2 and 3))

Obtaining the FI fraction 50 l of plasma are thawed at 0°±20° C. and centrifuged in order to obtain the cryoprecipitate. The pH of the plasma, which is low in cryoprecipitate, is brought to pH 7.2 with HCl, and ethanol is added (9±1%). The temperature is maintained at −2.5° C. After two hours of incubation, the suspension is centrifuged and a pellet (Cohn fraction I or FI) is obtained (±800 g).

The FI fraction is resuspended in citrate buffer (0.15M Na citrate—0.15M NaCl—pH 7.0±0.1) at 15° C. Alhydrogel (2% final concentration) is added and the incubation is continued at 22° C. for 20 minutes. After removing the pellet, which is rich in proteases, the supernatant is filtered through a clarifying filter (Pall 1 μm) at a flow rate of 1 l/m. A first viral inactivation is carried out by adding solvent/detergent (8 hours in the presence of 1% Tween 80 and 0.3% TNBP at 25° C.).

First glycine precipitation

After inactivation, the pH is adjusted to 6.1±0.1 and the glycine concentration is brought to 1M. After a minimum of 2 hours of precipitation at 4° C., the suspension is centrifuged or separated by decantation. The pellet is dissolved in 10 times its volume of citrate buffer at 30° C. and the pH is brought to 7.0±0.1.

Removal of the solvent/detergent by means of clarifying absorptive filtration

The suspension is filtered through charcoal of the AKS-4 or AKS-7 type (3 discs) and a filter of the EKSP kieselguhr type (3 discs) (flow rate: 700 ml/min).

The solvent/detergent is removed more efficiently through AKS-4 or AKS-7 charcoal filters such as those supplied by Zeiss than through "delipided" filters such as those supplied by Cuno.

Second glycine precipitation

The pH of the filtrate is brought to 6.1±0.1 and glycine is added (final concentration: 1M). The precipitation at 4° C. lasts for a minimum of 2.5 hours. The precipitate is obtained after centrifugation or decantation.

Second clarifying filtration

The pellet is dissolved in 3-times-diluted citrate buffer, and this solution is filtered as previously described.

Concentration and diafiltration

The filtrate from the second filtration is concentrated by ultrafiltration (Filtron®, Millipore) ("clotting assay") and subjected to diafiltration against 3-times-diluted citrate buffer.

Addition of stabilizers and second viral inactivation using ultraviolet rays

Stabilizers are added to the purified fibrinogen, the pH is adjusted to 7.0±0.1 and the solution of fibrinogen can be treated with UVC rays for the purpose of inactivating, in particular, non-enveloped viruses (parvovirus B19, hepatitis A and C viruses, etc.).

Sterilizing filtration

The solution is sterilized by filtration through 0.45 μm and 0.22 μm Millidisk® filters (Millipore).

Lyophilization and vigorous thermal treatment

After lyophilization, the fibrinogen can be heated at 80° C. for a period which is greater than or equal to 10 hours, preferably for a period of between 24 and 72 hours.

Results

The product which is obtained is characterized by the following properties:

- yield: from 0.4 to 1 g/l of starting plasma (FI fraction)
- effluent: 0.2 mg/l of plasma
- purity: greater than 98%
- high concentration of factor VIII (even after dry heating)
- absence of measurable proteases (in particular of vitamin K-dependent proteases)
- product soluble in less than 10 minutes
- product characterized by a very high degree of stability in solution: no coagulation after having been kept at 4° C. for more than 12 months
- very low production cost
- small decrease in the activity of the fibrinogen which has been subjected to three viral inactivations

TABLE 2

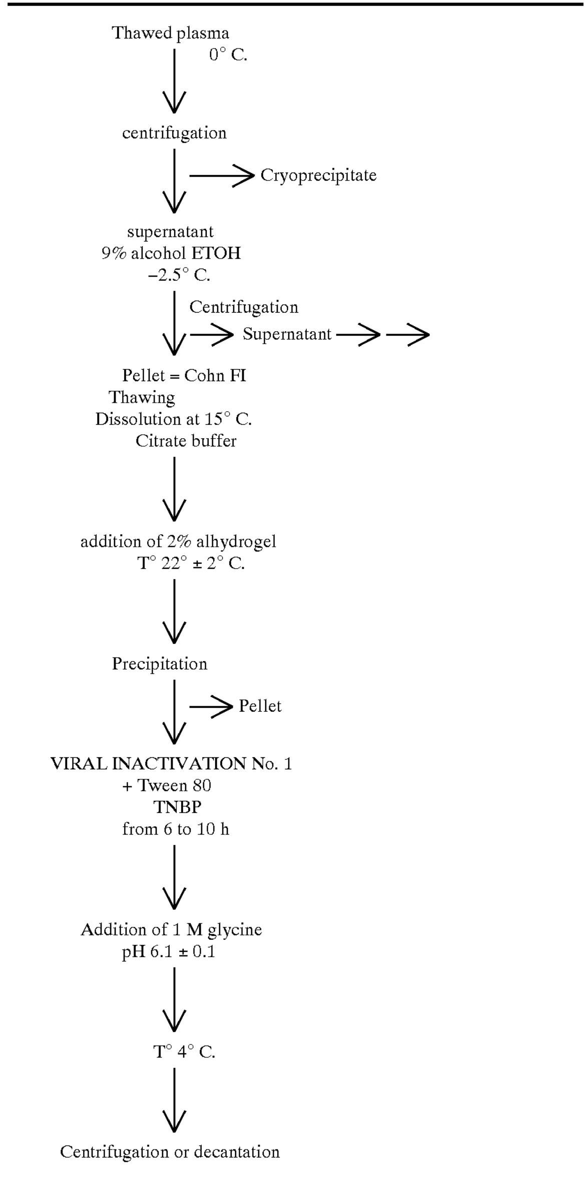

TABLE 3

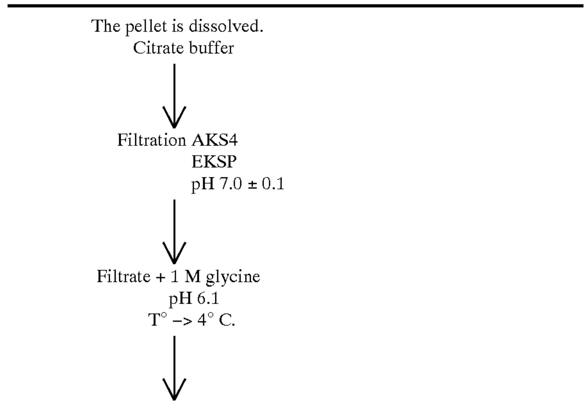

TABLE 3-continued

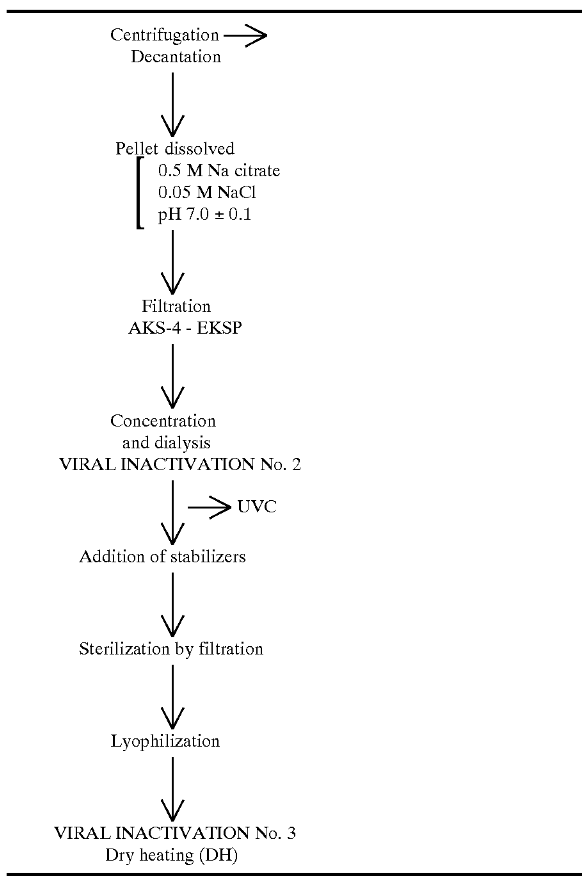

Plant for preparing the fibrinogen concentrate according to the invention

Figure 6:
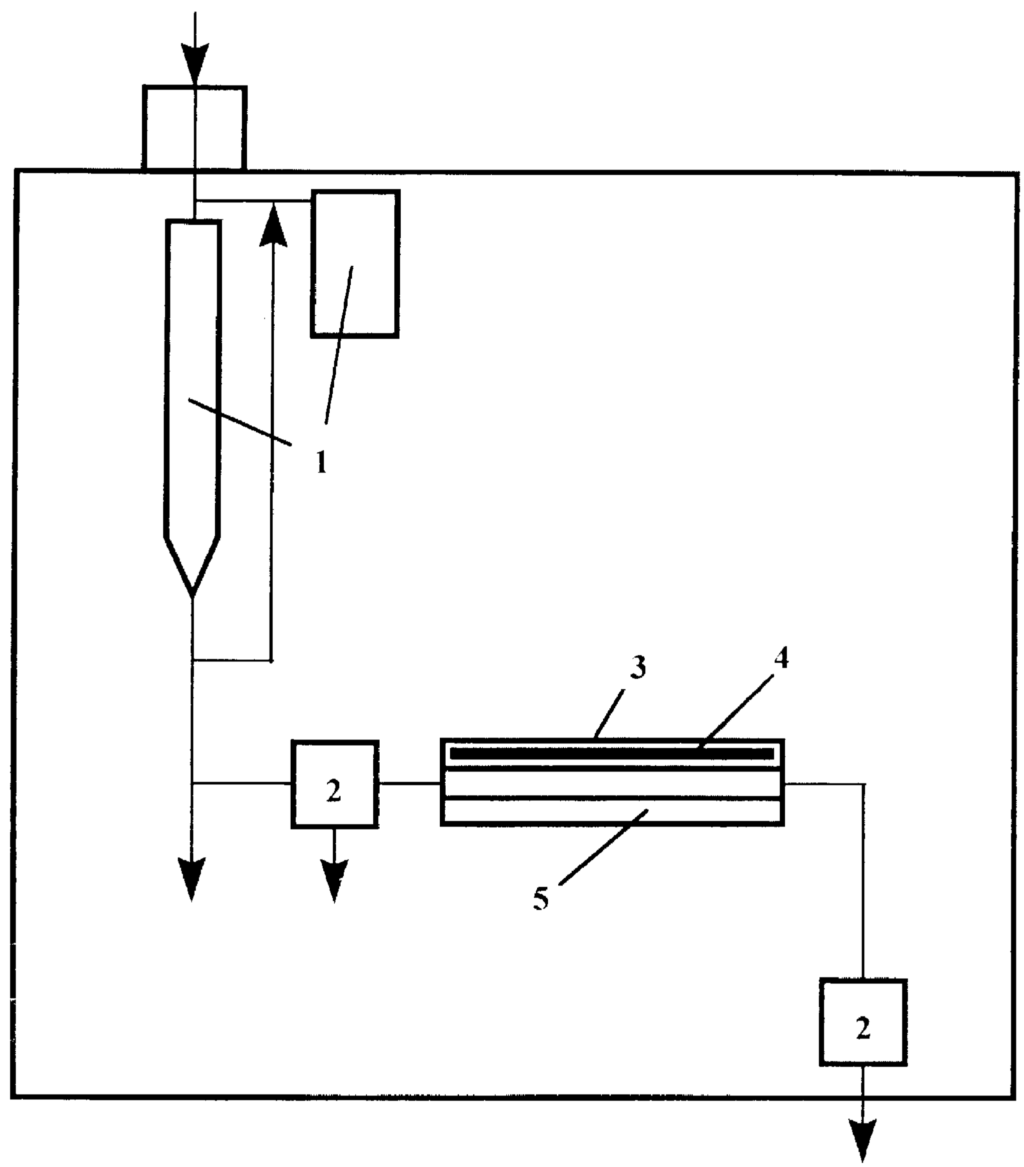
FIG. 6 diagrammatically represents a plant for preparing the fibrinogen concentrate according to the invention.

The appended FIG. 6 diagrammatically depicts a plant for preparing the fibrinogen concentrate according to the invention.

This plant includes devices (1 and 2) which effect precipitation, centrifugation/decantation, filtration, concentration and dialysis of the fibrinogen concentrate according to the invention and which can be adapted by the skilled person in accordance with the blood derivative being treated.

In addition, this plant includes a device (given reference number 3 in appended FIG. 6) which inactivates viruses in the blood derivative by means of a physical treatment.

The plant according to the present invention can therefore be employed for providing a physical viral inactivation treatment for any blood derivative, in particular coagulation factors (factor VIII, factor IX, etc.), immunoglobulins, albumin, fibrinogen, etc.

This device comprises a UV disinfection tube, more than 90% of whose emission is between 250 and 270 nm, preferably at 254 nm, and which is mounted in a reflecting enclosure which reflects the radiation towards a tube which is made of quartz or a polymerized material and which does not absorb in this wavelength range. No contact is possible between the product which is circulating in the tube 4 and the UV lamp 5.

A turbulence system, such as a baffle or an injection of nitrogen, renders it possible to maintain a homogeneous flow in the tube. The system for monitoring the quantity of UV which irradiates the tube is placed on the opposite side of the tube from the lamp. The dwell time of the product can be adjusted in order to obtain a constant dose of irradiation. The diameter of the tube can be adapted to the volume to be treated as can the power or the length of the disinfection lamp. The temperatures of both the interior of the enclosure and the liquid are monitored and recorded.

The whole system is made of materials which are in keeping with pharmaceutical good manufacturing practices (GMP), such as inox 304 stainless steel, Teflon, etc., and can be subjected to sanitary treatment in situ.

The use of such a UV radiation, in particular UVC radiation, system renders it possible to inactivate viruses, in particular non-enveloped viruses, especially single-strand viruses such as murine parvovirus (from 5 to 6 logs of viral inactivation).

The system is placed downstream of the process for preparing the blood derivative, for example prior to the sterilizing filtration or after the ultrafiltration.

The power of the UV lamp is between 18 and 132 watts. The activity of the preparations (factor VIII, fibrinogen and IgG) which are used is only slightly affected (5% reduction in activity on average).

The device can be constructed as one piece or as juxtaposed modules which are placed in series. While the irradiation doses vary between 100 and 2000 joules/m$^2$, they are preferably of the order of 250 joules/m$^2$.

The UV disinfection device which is employed in the plant according to the invention is of the s.p.1 type (AQUAFINE®, Valencia, Calif. (USA)).

EXAMPLE 5

Analysis of the Fibrinogen Concentrate According to the Invention

Table 4 provides an analysis of the characteristics of the fibrinogen concentrate which has been prepared from a solubilized plasma fraction consisting of the solubilized fraction of a plasma cryoprecipitate which has been subjected to a single step of chromatography on an ion exchange resin (chromato effluent), which fraction has, where appropriate, been treated by means of dry heating (DH chromato effluent) or obtained by treating the Cohn fraction I (FI), which fraction has, where appropriate, been treated by means of dry heating (DH FI).

This analysis demonstrates that the product which is obtained exhibits a purity which is particularly high, being greater than 98%, and exhibits very low proportions of solvents/detergents; the product nevertheless retains a substantial fraction of factor XIII, thereby enabling the fibrinogen concentrate according to the invention to be applied as a biological adhesive.

TABLE 4

| Starting fraction | Purity (%) | mg FXIII/1 | ppm Tween 80 | ppm TNBP |
|---|---|---|---|---|
| Chromato effluent | >98 | 35 | 13 | <0.5 |
| DH chromato effluent | >98 | 0.7 | 17 | <0.5 |
| FI | >98 | 360 | <10 | <0.5 |
| DH FI | >98 | 103 | <10 | <0.5 |

DH: dry heat

We claim:

1. A fibrinogen concentrate having a purity higher than 98% and being free of viral contaminants and proteases.

2. A fibrinogen concentrate according to claim 1, wherein said fibrinogen concentrate is delipidated.

3. A fibrinogen concentrate according to claim 1, wherein said fibrinogen concentrate has a characteristic of not coagulating as measured when being kept at a temperature of 4° C. for longer than 12 months.

4. A process for obtaining a fibrinogen concentrate, comprising the steps of:

subjecting a solubilized plasma fraction containing fibrinogen to a viral inactivation chemical treatment using a solvent/detergent;

subjecting the resulting viral-inactivated fraction to precipitation in a solution containing an amino acid at an acidic pH to obtain a supernatant;

filtering the supernatant to obtain a purified fibrinogen concentrate; and recovering the purified fibrinogen concentrate, said purified fibrinogen concentrate having a purity higher than 98% and being free of viral contaminants and proteases.

5. A process according to claim 4, wherein said amino acid is glycine.

6. A process according to claim 4, wherein said filter is an activated carbon filter.

7. A process according to claim 4, wherein the pH of said solution is between 4.0 and 7.0.

8. A process according to claim 7, wherein said pH is between 5.5 and 6.5.

9. A process according to claim 4, wherein the amino acid concentration in said solution is between 0.1 and 3.3 molar.

10. A process according to claim 9, wherein the amino acid concentration in said solution is between 0.5 and 1.5 molar.

11. A process according to claim 4, further comprising a viral inactivation physical treatment wherein said solubilized plasma fraction is at least either heated at a temperature of 80° C. or higher for at least 10 hours, or irradiated with ultraviolet C rays having wavelengths between 250 nm and 270 nm at an irradiation dose of about 250 joules/$m^2$.

12. A process according to claim 4, wherein said solubilized plasma fraction is selected from the group consisting of the solubilized fraction of plasma cryoprecipitate, the Cohn FI fraction, and a mixture of the foregoing.

13. A process according to claim 12, wherein the solubilized fraction of plasma cryoprecipitate has been subjected to a single step of chromatography on an ion exchange resin to retain the factor VIII/von Willebrand factor complex.

14. A process according to claim 13, wherein said ion exchange resin comprises a matrix of a gel capable of retaining the factor VIII/von Willebrand factor complex due to its porosity and hydrophobicity properties.

15. A process according to claim 12, wherein the solubilized fraction of plasma cryoprecipitate has been subjected to at least either a prepurification treatment comprising a treatment with aluminum hydroxide or a precipitation treatment at a temperature of between 10° C. and 20° C.

16. A composition comprising a fibrinogen concentrate having a purity higher than 98% and being free of viral contaminants and proteases, said fibrinogen concentrate being in a form suitable for said composition.

* * * * *